United States Patent [19]
Zamboni et al.

[11] Patent Number: 5,817,645
[45] Date of Patent: Oct. 6, 1998

[54] PHARMACEUTICAL COMPOSITIONS CONTAINING LOW MOLECULAR WEIGHT DERMATAN SULFATE FOR THE THERAPY OF PULMONARY EMBOLISM

[75] Inventors: Villiam Zamboni; Maria Barbanti, both of Bologna; Claudia Baldazzi, Ozzano Emilia, all of Italy

[73] Assignee: Alfa Wassermann S.p.A., Alanno, Italy

[21] Appl. No.: 764,486

[22] Filed: Dec. 12, 1996

[30] Foreign Application Priority Data

Jan. 16, 1996 [IT] Italy ................................. BO96A0018

[51] Int. Cl.$^6$ ...................... A61K 31/715; A61K 31/725
[52] U.S. Cl. ................. 514/54; 514/56; 514/822
[58] Field of Search ................... 424/422, 400; 514/56, 54, 937, 822

[56] References Cited

U.S. PATENT DOCUMENTS

| | | | |
|---|---|---|---|
| 4,973,580 | 11/1990 | Mascellani et al. | 514/54 |
| 5,164,378 | 11/1992 | Conti et al. | 514/56 |
| 5,252,339 | 10/1993 | Cristofori et al. | 424/479 |
| 5,576,304 | 11/1996 | Kakkar et al. | 514/56 |
| 5,763,427 | 6/1998 | Weitz et al. | 514/56 |

OTHER PUBLICATIONS

Bergqvist et al. Glycosaminoglycans in Prophylaxis Against Venous Thromboembolism. Advances in Experimental Medicine & Biology. vol. 313, pp. 259–274. (1992).

Cohen et al. A Dose Ranging Study of Evaluate Dermatan Sulphate in Preventing Deep Vein Thrombosis Following Total Hip Arthroplasty. Thrombosis and Haemostasis. 72(6), pp. 793–798.(1994).

Charbonnier et al. Anticoagulant Therapy in Pulmonary Embolism. Archives des Maladies du Coeur et des Vaisseaux. vol. 88, No. 11(supplemental), pp. 1755–1761. (Nov. 1995).

Gent et al. Low–Molecular Wt. Heparinoid Orgaran is More Effective Than Aspirin in the Prevention of Venous Thromboembolism After Surgery for Hip Fracture. Circulation. 93(1), pp. 80–84. (Jan. 1996).

*Primary Examiner*—Robert H. Harrison
*Attorney, Agent, or Firm*—Bucknam and Archer

[57] ABSTRACT

The prevention and therapy of pulmonary embolism with pharmaceutical compositions containing low molecular weight dermatan sulfate is described. These pharmaceutical compositions are administered by subcutaneous, intramuscular or intravenous route at a daily dosage between 200 and 3000 mgs of active principle. The low molecular weight dermatan sulfate preferred in carrying out the invention has an average molecular weight equal to 5500±1100 Daltons and is obtained by depolymerization of the dermatan sulfate of natural origin in the presence of hydrogen peroxide and cupric ions.

4 Claims, No Drawings

PHARMACEUTICAL COMPOSITIONS CONTAINING LOW MOLECULAR WEIGHT DERMATAN SULFATE FOR THE THERAPY OF PULMONARY EMBOLISM

FIELD OF THE INVENTION

This invention relates to prevention and treatment of pulmonary embolism.

BACKGROUND OF THE PRIOR ART

The pulmonary embolism is a pathology of remarkable clinical and socioeconomical importance which comes up as serious complication of the deep venous thrombosis and represents the more common cardiovascular disease after the ischaemic heart diseases and the stroke [Giuntini C. et al., Chest 107, 3S–9S (1995)], with an incidence growing with the age [Kniffin W. D. Jr, et al., Arch. Int. Med. 154, 861–6 (1994)]. Every year it causes only in the United States about 50000 cases of death [Kniffin W. D. Jr, et al., Arch. Int. Med. 154, 861–6 (1994)] and 250000 hospitalizations [Anderson F. A. Jr, et al., Arch. Int. Med. 151, 933–8 (1991)]. The pulmonary embolism can be both primary or idiopathic and secondary; in this latter case it is mainly subsequent to surgical operations or to traumas but it can come also from cardiovascular, tumoral and systemic diseases [Giuntini C., et al., Chest 107, 3S–9S (1995)].

The pulmonary embolism is often asymptomatic and frequently it is not diagnosed, as the post-mortem examinations show, also because the diagnostic methods at present available are insufficiently used because they are complicated, expensive and scarcely sensitive [Agnelli G., Chest 107, 39S–43S, (1995)]. The invariability of the death rate in the last 30 years [Lilienfeld D. E., et al., Chest 98, 1067–72, (1990)] is an evident index of the poor present ability to face in an efficacious manner this kind of pathology and in particular of the lack of a reliable and safe pharmacological therapy. The anticoagulants, like heparin, low molecular weight heparins and warfarin, because of their ability to prevent the formation of new thrombi and to stop the growth of those existing, are the drugs more commonly used in the prevention and cure of the pulmonary embolism [Stein P. D., Clinics in Chest Medicine 16, 229–33, (1995)]. The thrombolytic drugs, like urokinase, that carry out a progressive action of dissolution of the thrombus, are less used. The use of the anticoagulants and also more that of the thrombolytic drugs is coupled to a very high risk of hemorrhages, as the people skilled in the field know. Moreover the great differences of individual pharmacokinetic response make necessary the continuous check at hospital level, except for the low molecular weight heparins. The anticoagulants and the thrombolytic drugs at present available are used notwithstanding the risks and the complexity of use because first choice drugs totally lack in the therapy of the pulmonary embolism.

By considering the present state of the art, a product able to carry out an activity more effective than that of the present anticoagulant and thrombolytic drugs and to protect the patients from the hemorrhagic risk by virtue of a different mechanism of action clearly represents a substantial advance in the prevention and therapy of the pulmonary embolism. A drug of this kind can in fact be used with a confidence and a safety of use surely higher than that of the drugs at present on the market.

The fractions of the dermatan sulfate having low molecular weight, coming from the depolymerization of the dermatan sulfate of natural origin have now been found endowed with proper pharmacological characteristics so as to be used for the prevention and therapy of the pulmonary embolism. In particular, these characteristics that can be defined optimal have been found in the low molecular weight dermatan sulfate having a range of molecular weights between 4000 and 8000 Daltons and an average molecular weight equal to 5500±1100 Daltons obtained by depolymerization of the dermatan sulfate of natural origin in the presence of hydrogen peroxide and cupric ions as described in European Patent EP 0221977. The low molecular weight dermatan sulfate showed, besides the good pharmacological activity, lack of side effects of hemorrhagic type both in the animal [Barbanti M. et al., Thromb. Haemost. 69, 147–151, (1993)] and in man [Dettori A. G. et al., Sem. Thromb. Hemost. 20, 259–265, (1994) and Thromb. Res. 79 (3), 249–260, (1995) and Traini A. M. et al., J. Int. Med. Res. 22, 323–331, (1994)]. Finally, the low molecular weight dermatan sulfate showed a bioavailability higher than that of the other glycosaminoglycans and in particular higher than the natural dermatan sulfate, with respect to which it shows a better absorption both by subcutaneous and intramuscular route and a more protracted pharmacokinetic also by intravenous administration [Dawes J., Thromb. Haemostasis 69, 339–43 (1993)]. The low molecular weight dermatan sulfate has been preferrred as drug because of these reasons even though the natural dermatan sulfate could equally be used in the treatment of the pulmonary embolism.

SUMMARY OF THE INVENTION

An object of the present invention is the use of therapeutically effective amounts of low molecular weight dermatan sulfate and of the pharmaceutical compositions containing it in the prevention and therapy of the pulmonary embolism. The low molecular weight dermatan sulfate having a range of molecular weights between 4000 and 8000 Daltons and an average molecular weight equal to 5500±1100 Daltons obtained by depolymerization of the dermatan sulfate of natural origin in the presence of hydrogen peroxide and cupric ions as described in the European Patent EP 0221977 is used and exemplified in the realization of the invention. The use of this type of low molecular weight dermatan sulfate is clearly illustrative and absolutely not limitative of the invention. The invention is supported by the efficacy shown by the use of the low molecular weight dermatan sulfate in a pharmacological test carried out on animals and in a clinical trial on patients suffering from pulmonary embolism.

The pharmacological test has been carried out in the rat by causing the formation of a pulmonary embolus by injecting a clot of radioactive blood in a jugular vein according to the method of Clozel S. P. et al., J. Cardiovasc. Pharmacol. 12, 520–5, (1988). The rats have been treated, by injection in a femoral vein, with 50 mg/kg of low molecular weight dermatan sulfate or/with a physiological solution not containing the active principle immediately after the inoculation of the radioactive clot. The ability of causing the lysis of the pulmonary embolus due to the active principle has clearly emerged from the difference of the remaining radioactivity measured in the treated animals in respect with that measured in the untreated control animals. The clinical trial has been carried out by treating by intravenous route with 1200 mg/die of low molecular weight dermatan sulfate for a period of time of ten days eight patients in whom the phleboscintigraphy had shown a situation of serious bilateral pulmonary hypoperfusion showing pulmonary embolism. The therapeutic effectiveness of the active principle has been evaluated on the basis of the comparison between the degree of pulmonary perfusion found by means of the phleboscintigraphy at the end of the treatment and that shown at the beginning of the treatment. The clinical trial showed the effectiveness of the active principle in 7 out of 8 patients, with a remarkable improvement of the pulmonary reperfusion and without any hemorrhagic complication. These data fully support the therapeutic use of the low molecular weight dermatan sulfate in the prevention and therapy of the pulmonary embolism. All kinds of pharmaceutical compositions administrable by the subcutaneous, intramuscular or intravenous routes containing as active principle a low molecular weight dermatan sulfate are medicines useful in carrying out the present invention. The pharmaceutical compositions administrable by the subcutaneous, intramuscular or intravenous routes containing as active principle low molecular weight dermatan sulfate having a range of molecular weights between 4000 and 8000 Daltons and an average molecular weight equal to 5500±1100 Daltons obtained by depolymerization of the dermatan sulfate of natural origin in the presence of hydrogen peroxide and cupric ions as described in European Patent EP 0221977 are preferred within the scope of the present invention.

The daily dosage depends on the body weight and the seriousness of the pathology and is comprised between 200 and 3000 mgs, preferably between 800 and 1600 mgs, of low molecular weight dermatan sulfate.

The examples underneath reported are a further illustration of the invention and do not have to be taken as an its limitation.

EXAMPLE 1
Thrombolytic Treatment with Low Molecular Weight Dermatan Sulfate in Rat Male Sprague Dawley rats weighing 250–300 g have been shared in three groups of 24–29 animals. The formation of the pulmonary embolus has been produced by means of injection of a radioactive blood clot, prepared in vitro, in a jugular vein as described by Clozel J. P. et al., J. Cardiovasc. Pharmacol. 12, 520–5, (1988). Immediately after the inoculation of the radioactive clot, half rats of each group have been administered by intravenous route into the femoral vein with 50 mg/kg of low molecular weight dermatan sulfate having average molecular weight equal to 5500±1100 Daltons manufactured according to European Patent EP 0221977 (treated rats), while the other half rats have been administered with a physiologic solution without active principle (control rats) in the same manner. The radiometric measurement, carried out on the three groups respectively after 30, 60 and 120 minutes, allows to compare the difference between the lysis of the pulmonary embolus caused by the active principle (treated rats) and the spontaneous lysis (control rats). The data obtained, show how the treatment with low molecular weight dermatan sulfate caused a significant lysis of the pulmonary embolus at all the times taken into consideration.

EXAMPLE 2
Treatment of Patients Suffering from Pulmonary Embolism with Low Molecular Weight Dermatan Sulfate.

Eight patients, selected on the basis of a phleboscintigraphic diagnosis of pulmonary embolism have been treated by intravenous route with 1200 mg a day, for a period of 10 days, of low molecular weight dermatan sulfate having a range of molecular weights between 4000 and 8000 Daltons and an average molecular weight equal to 5500±1100 Daltons obtained as described in European Patent EP 0221977. The instrumental scintigraphic measure that has allowed to evaluate the modification of the pulmonary circulation has been repeated at the end of the therapy making possible the comparison between the situations recorded before and after the therapy. The comparative examination of the phleboscintigraphies carried out before and after the treatment has shown how 7 out of 8 patients showed a remarkable improvement of the pulmonary reperfusion ascribable to a revascularization of the pulmonary portion affected by the embolism; only in one case out of 8 cases no difference has been recorded.

Therefore the experimental data have clearly shown the effectiveness of the treatment with low molecular weight dermatan sulfate and moreover no hemorrhagic complication has been shown in the treated patients.

TABLE 1
Effect of low molecular weight dermatan sulfate on the lysis of thrombi in rats with pulmonary embolism
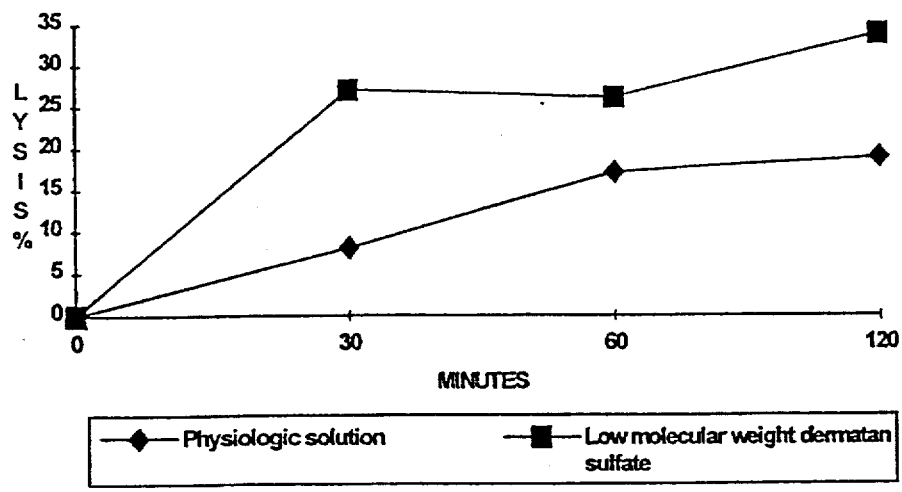

We claim:

1. A method of therapy of pulmonary embolism which consists of administering to a patient in need thereof a pharmaceutical composition in unit dosage form containing low molecular weight dermatan sulfate in the amount of 200–3000 mgs per dose.

2. The method according to claim 1 wherein said pharmaceutical composition is administered by subcutaneous, intramuscular or intravenous route.

3. The method according to claim 1 wherein the total daily dose of low molecular weight dermatan sulfate is 200–3000 mg.

4. The method according to claim 1 wherein said low molecular weight dermatan sulfate has a range of molecular weights between 4000 and 8000 Daltons and an average molecular weight equal to 5500±1100 Daltons and is obtained by depolymerization of the dermatan sulfate of natural origin in the presence of hydrogen peroxide and cupric ions.

* * * * *

UNITED STATES PATENT AND TRADEMARK OFFICE
CERTIFICATE OF CORRECTION

PATENT NO.   :   5,817,645
DATED        :   October 6, 1998
INVENTOR(S)  :   William Zamboni, et al It is certified that error appears in the above-indentified patent and that said Letters Patent is hereby corrected as shown below:

Col. 4, line 1

(control rats). The data obtained, reported in Table 1, submitted in Fig. 1, show how the treatment . . .

Table 1 to be attached to the patent
as per attached copy

Signed and Sealed this

Twenty-sixth Day of October, 1999

Attest:

Attesting Officer

Q. TODD DICKINSON

Acting Commissioner of Patents and Trademarks